(12) United States Patent
Orihashi et al.

(10) Patent No.: US 9,164,112 B2
(45) Date of Patent: Oct. 20, 2015

(54) AUTOMATIC ANALYZER

(75) Inventors: Toshihide Orihashi, Hitachinaka (JP); Masaki Takano, Tokyo (JP); Mariko Miyaki, Tokyo (JP); Tatsuya Tokunaga, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 451 days.

(21) Appl. No.: 13/059,510

(22) PCT Filed: Aug. 28, 2009

(86) PCT No.: PCT/JP2009/065452
§ 371 (c)(1),
(2), (4) Date: Mar. 21, 2011

(87) PCT Pub. No.: WO2010/027037
PCT Pub. Date: Mar. 11, 2010

(65) Prior Publication Data
US 2011/0169836 A1    Jul. 14, 2011

(30) Foreign Application Priority Data
Sep. 3, 2008   (JP) ................... 2008-225428

(51) Int. Cl.
G06F 17/00        (2006.01)
G01N 35/00        (2006.01)

(52) U.S. Cl.
CPC .. *G01N 35/00722* (2013.01); *G01N 2035/0091* (2013.01)

(58) Field of Classification Search
CPC ............. G06T 11/00; G01N 35/00722; G01N 2035/0091
USPC .......................................................... 715/253
See application file for complete search history.

(56) References Cited

U.S. PATENT DOCUMENTS

| 6,269,276 | B1 | 7/2001 | Akhavan et al. | |
|---|---|---|---|---|
| 7,188,317 | B1 * | 3/2007 | Hazel | 715/804 |
| 7,444,599 | B1 * | 10/2008 | Chaudhri et al. | 715/830 |
| 8,347,228 | B1 * | 1/2013 | Kates et al. | 715/821 |
| 8,689,129 | B1 * | 4/2014 | Kumar et al. | 715/777 |
| 2002/0165937 | A1 * | 11/2002 | Nitta et al. | 709/217 |
| 2004/0030578 | A1 * | 2/2004 | Cross et al. | 705/2 |
| 2004/0070627 | A1 * | 4/2004 | Shahine et al. | 345/794 |
| 2004/0091396 | A1 * | 5/2004 | Nakamura et al. | 422/65 |
| 2004/0130568 | A1 * | 7/2004 | Nagano et al. | 345/733 |
| 2005/0013736 | A1 | 1/2005 | McKeever | |

(Continued)

FOREIGN PATENT DOCUMENTS

| JP | 01-128089 A | 5/1989 |
|---|---|---|
| JP | 03-269487 A | 12/1991 |

(Continued)

*Primary Examiner* — Scott Baderman
*Assistant Examiner* — Mustafa Amin
(74) *Attorney, Agent, or Firm* — Mattingly & Malur, PC

(57) ABSTRACT

A display is provided for an automatic analyzer to display statistics such as measurement results. A width of a display in a window that displays statistics may be adjusted and the amount of information to be displayed on the display is changed according to a level of detail of the information which the operator wants to confirm. Sample information, measurement results, and detailed information related to the measurement results are simultaneously displayed without a subwindow being displayed in overlapped form in the limited display area.

3 Claims, 7 Drawing Sheets

601

| DETAIL LEVEL | WIDTH | LIST LENGTH | DISPLAY MODE | DISPLAY ITEMS |
|---|---|---|---|---|
| HIGH | 150 | 200 | SAMPLE DETAILS | SAMPLE MEASUREMENT STATUS, SAMPLE ID, SAMPLE NAME, AND SAMPLE SETUP POSITION NUMBER |
| MIDDLE | 100 | 200 | — | SAMPLE MEASUREMENT STATUS, SAMPLE ID, AND SAMPLE NAME |
| LOW | 50 | 200 | MEASUREMENT RESULT DETAILS / MEASUREMENT-RELATED DETAILS | SAMPLE MEASUREMENT STATUS AND SAMPLE ID |

SAMPLE LIST DEFINITION TABLE

602

| DETAIL LEVEL | WIDTH | LIST LENGTH | DISPLAY MODE | DISPLAY ITEMS |
|---|---|---|---|---|
| HIGH | 200 | 200 | MEASUREMENT RESULT DETAILS | ANALYTICAL ITEM NAME, FIRST TEST VALUE, RETEST VALUE, FIRST-TEST DATA ALARM, RETEST DATA ALARM, SAMPLE-DISPENSING TIME RELATING TO FIRST TEST VALUE, AND SAMPLE-DISPENSING TIME RELATING TO RETEST VALUE |
| MIDDLE | 100 | 200 | SAMPLE DETAILS | ANALYTICAL ITEM NAME, FIRST TEST VALUE, RETEST VALUE, FIRST-TEST DATA ALARM, AND RETEST DATA ALARM |
| LOW | 50 | 200 | MEASUREMENT-RELATED DETAILS | ANALYTICAL ITEM NAME, FIRST TEST VALUE, AND RETEST VALUE |

MEASUREMENT RESULT LIST DEFINITION TABLE

(56) References Cited

U.S. PATENT DOCUMENTS

| | | |
|---|---|---|
| 2005/0138160 A1* | 6/2005 | Klein et al. .................... 709/223 |
| 2007/0130538 A1* | 6/2007 | Chiu .............................. 715/792 |
| 2007/0168859 A1* | 7/2007 | Fortes ........................... 715/700 |
| 2007/0180401 A1* | 8/2007 | Singh et al. ................... 715/794 |
| 2008/0021755 A1* | 1/2008 | Jones et al. ....................... 705/8 |
| 2008/0065420 A1* | 3/2008 | Tirinato et al. ................... 705/3 |
| 2008/0148166 A1* | 6/2008 | Brunswig et al. ............. 715/766 |
| 2009/0074618 A1* | 3/2009 | Mizumoto et al. ........... 422/68.1 |
| 2009/0204440 A1* | 8/2009 | Stroup et al. ...................... 705/3 |
| 2011/0136684 A1* | 6/2011 | Heiner et al. ..................... 506/7 |
| 2011/0163968 A1* | 7/2011 | Hogan ........................... 345/173 |
| 2011/0238435 A1* | 9/2011 | Rapaport et al. .................. 705/2 |
| 2011/0289397 A1* | 11/2011 | Eastmond et al. ............ 715/212 |
| 2012/0004742 A1* | 1/2012 | Wakamiya et al. ............. 700/15 |
| 2012/0197538 A1* | 8/2012 | Cross et al. ..................... 702/19 |
| 2013/0002847 A1* | 1/2013 | Zahniser et al. ................ 348/79 |

FOREIGN PATENT DOCUMENTS

| | | |
|---|---|---|
| JP | 08-314677 A | 11/1996 |
| JP | 09-211003 A | 8/1997 |
| JP | 11-272382 A | 10/1999 |
| JP | 11-337555 A | 12/1999 |
| JP | 2000-321281 A | 11/2000 |
| JP | 2007-524083 A | 8/2007 |
| JP | 2008-052580 A | 3/2008 |
| JP | 2008-058129 A | 3/2008 |

* cited by examiner

FIG.2

| St. | ID | Name | Pos | | Test | 1st | Alarm | Rerun | Alarm |
|---|---|---|---|---|---|---|---|---|---|
| P | 001 | ONO TARO | 1 | | Ca | 5.0 | L | 7.0 | |
| C | 002 | MORI MIHO | 2 | | TP | 6.0 | | 9.0 | H |
| O | 003 | HORI KEN | 3 | | | | | | |
| C | 004 | TODA KUMI | 4 | | | | | | |

DETAIL

FIG.3

| St. | ID | | Test | 1st | Alarm | Time | Rerun | Alarm | Time |
|---|---|---|---|---|---|---|---|---|---|
| P | 001 | | Ca | 5.0 | L | 12:00 | 7.0 | | 12:11 |
| C | 002 | | TP | 6.0 | | 12:01 | 9.0 | H | 12:13 |
| O | 003 | | | | | | | | |
| C | 004 | | | | | | | | |

MONITOR
REAGENT
CALI-BRATION

| DETAIL LEVEL | WIDTH | LIST LENGTH | DISPLAY MODE | DISPLAY ITEMS |
|---|---|---|---|---|
| HIGH | 150 | 200 | SAMPLE DETAILS | SAMPLE MEASUREMENT STATUS, SAMPLE ID, SAMPLE NAME, AND SAMPLE SETUP POSITION NUMBER |
| MIDDLE | 100 | 200 | — | SAMPLE MEASUREMENT STATUS, SAMPLE ID, AND SAMPLE NAME |
| LOW | 50 | 200 | MEASUREMENT RESULT DETAILS  MEASUREMENT -RELATED DETAILS | SAMPLE MEASUREMENT STATUS AND SAMPLE ID |

SAMPLE LIST DEFINITION TABLE

602

| DETAIL LEVEL | WIDTH | LIST LENGTH | DISPLAY MODE | DISPLAY ITEMS |
|---|---|---|---|---|
| HIGH | 200 | 200 | MEASUREMENT RESULT DETAILS | ANALYTICAL ITEM NAME, FIRST TEST VALUE, RETEST VALUE, FIRST-TEST DATA ALARM, RETEST DATA ALARM, SAMPLE -DISPENSING TIME RELATING TO FIRST TEST VALUE, AND SAMPLE-DISPENSING TIME RELATING TO RETEST VALUE |
| MIDDLE | 100 | 200 | SAMPLE DETAILS | ANALYTICAL ITEM NAME, FIRST TEST VALUE, RETEST VALUE, FIRST-TEST DATA ALARM, AND RETEST DATA ALARM |
| LOW | 50 | 200 | MEASUREMENT -RELATED DETAILS | ANALYTICAL ITEM NAME, FIRST TEST VALUE, AND RETEST VALUE |

MEASUREMENT RESULT LIST DEFINITION TABLE

| DETAIL LEVEL | WIDTH | LIST LENGTH | DISPLAY MODE | DISPLAY ITEMS |
|---|---|---|---|---|
| HIGH | 150 | 200 | SAMPLE DETAILS | SAMPLE MEASUREMENT STATUS, SAMPLE ID, SAMPLE NAME, AND SAMPLE SETUP POSITION NUMBER |
| MIDDLE | 100 | 200 | — | SAMPLE MEASUREMENT STATUS, SAMPLE ID, AND SAMPLE NAME |
| LOW | 50 | 100 | MEASUREMENT RESULT DETAILS MEASUREMENT-RELATED DETAILS | SAMPLE MEASUREMENT STATUS AND SAMPLE ID |

SAMPLE LIST DEFINITION TABLE

902

| DETAIL LEVEL | WIDTH | LIST LENGTH | DISPLAY MODE | DISPLAY ITEMS |
|---|---|---|---|---|
| HIGH | 200 | 200 | MEASUREMENT RESULT DETAILS | ANALYTICAL ITEM NAME, FIRST TEST VALUE, RETEST VALUE, FIRST-TEST DATA ALARM, RETEST DATA ALARM, SAMPLE-DISPENSING TIME RELATING TO FIRST TEST VALUE, AND SAMPLE-DISPENSING TIME RELATING TO RETEST VALUE |
| MIDDLE | 100 | 200 | SAMPLE DETAILS | ANALYTICAL ITEM NAME, FIRST TEST VALUE, RETEST VALUE, FIRST-TEST DATA ALARM, AND RETEST DATA ALARM |
| LOW | 100 | 100 | MEASUREMENT-RELATED DETAILS | ANALYTICAL ITEM NAME, FIRST TEST VALUE, RETEST VALUE, FIRST-TEST DATA ALARM, AND RETEST DATA ALARM |

MEASUREMENT RESULT LIST DEFINITION TABLE

AUTOMATIC ANALYZER

TECHNICAL FIELD

The present invention relates generally to automatic analyzers that measure component concentrations in a sample containing blood, urine, and/or the like. More particularly, the invention is directed to an automatic analyzer provided with a window function to display measurement results.

BACKGROUND ART

Automatic analyzers that measure component concentrations in a sample containing blood, urine, and/or the like, are of complex window composition associated with functional diversification. In order to enable immediate recognition of analyzer operation or rapid response to analyzer-related alarms, these automatic analyzers make a continuous window display of their operational status information. Display areas other than the continuous window display area, therefore, are limited in size, which makes it necessary to display sample information and measurement results in the limited display areas. In addition, these automatic analyzers employ a touchpanel as an operating window so that an operator can perform window operations even with a container or vessel or the like in one hand or easily perform window operations in a standing posture. This requires the window to be composed of the display parts, such as buttons and scrollbars, that are suitably sized to enable the touchpanel operations, and thus limits the amount of information which can be displayed at one time.

A window for presenting a time-varying display of detailed information on such measurement results as absorbance, is disclosed in Patent Document 1 as a way to display detailed information on reaction processes and reagents related to the measurement results.

LITERATURE ON RELATED ART

Patent Documents

Patent Document 1: JP-2000-321281-A

SUMMARY OF THE INVENTION

Problems to be Solved by the Invention

In the foregoing conventional technique, for example in case of an alarm related to the measurement results, seeking for causes of the alarm requires an operator to use independent windows to confirm the reaction process data, calibration curves, reagent information, and other detailed information relating to the sample and its measurement results. This has laid a heavy burden upon the operator during such alarm cause seeking based on multiple kinds of detailed measurement result information. In addition, to sequentially confirm detailed measurement result information on a plurality of analytical items or confirm a plurality of kinds of detailed information in order to confirm any changes in data that occur before and after reagent bottle changes, it is necessary for the operator to alternate between window display of the measurement results and that of the detailed information, with each selection of a display item or window. These operations requiring a large number of operating steps have also heavily burdened the operator.

Furthermore, the window for displaying the detailed information is commonly displayed in overlapped form as a subwindow upon the measurement result display window, so it has been difficult for the operator, while displaying the detailed measurement result window, to confirm in real time any changes in measurement status of a sample if inquired of as to the measurement status of the sample from a doctor.

Furthermore, because of the limited window display areas, there has been no way available for the operator, while displaying sample or measurement result information at the same time, to display all necessary information at a time without opening a subwindow, by changing a display method according to a desired detail level of information.

In addition, cases of analyzers being operated by inexperienced users, except in the presence of a specialized medical technologist, are increasing, backed by the curtailment of medical expenses and the complexity of window composition due to functional diversification. With these and other situations behind, it is being required of automatic analyzers to have the window composition that is free from the need to change the window to other windows frequently and enables easy operations and rapid response to measured-data alarms.

An object of the present invention is to provide an automatic analyzer including an operating window minimized in the number of operating steps and window changes required for an operator to take to confirm detailed information on measurement results, the operating window further being composed to facilitate seeking for causes of measured-data alarms and thus to reduce a burden upon the operator.

Means for Solving the Problems

In order to solve the foregoing problems, an operating window of an automatic analyzer according to the present invention is composed as follows:

In addition to means that displays detailed contents over multiple categories, the automatic analyzer includes control means that includes a definition table in which a priority level relating to displaying one of multiple display items is stored in advance for each of the categories; wherein, if two or more of the categories are specified to be displayed, the control means controls the display in accordance with the priority level prestored in the definition table so that all specified category items are displayed in one window without any of the specified category items being overwritten.

The multiple categories here are, for example, a sample list, a measurement result list, a reaction process monitor, and the like. However, these can be other categories if the display items have been divided according to kind.

An independent priority level for display may or may not be assigned to each display item. If the display items need prioritizing, the respective priority levels may be represented using numbers, for example "1, 2, etc. up to a maximum necessary number", or using alphabetic characters, for example "the highest assignable level, the next highest assignable level, etc. up to the lowest assignable level". If the display items need no prioritizing, a detail level of display may, for example, be represented according to the amount of information. For example, four display items may be displayed for a high level of detail, three items for a middle level of detail, or one item for a low level of detail.

In addition, "all specified category items are displayed in one window without any of the specified category items being overwritten" refers to a concept that encompasses a case in which a new display window opens as a subwindow in overlapped form on one display window and displays other data or information, and a case in which the display window is replaced by another display window and other data or information is displayed on this window.

A more preferred aspect is described below.

An operating window in the more preferred aspect first includes a sample list that displays a list of samples. The sample list contains display items such as a sample identification code (ID), sample name, sample setup position number, sample measurement status, and more. The operating window also includes a measurement result list that displays a list of measurement results relating to a sample which has been selected in the sample list. The measurement result list contains several display items, which are first test values and retest values relating to individual analytical items for the sample selected in the sample list, data alarms that denote existence and causes of measurement result abnormality, and other information. The above two lists are displayed in a definite window display area at the same time. Upon an operator performing window operations for confirming detailed information on a sample, a current mode changes to a sample details mode and width of the sample list and that of the measurement result list are increased and reduced, respectively, in accordance with previously assigned display items and definition information on the widths of the lists. After this, the two lists are simultaneously displayed to stay in the definite window display area. Upon the operator performing window operations for confirming detailed information on measurement results, the width of the sample list and that of the measurement result list are reduced and increased, respectively, in accordance with the previously assigned display items and definition information on the widths of the lists.

Additionally, upon the operator performing window operations for confirming the absorbance (reaction process data) that has been used to calculate a concentration which forms part of the measurement results, the widths of the sample list and the measurement result list are reduced and the two lists and a reaction process monitor are simultaneously displayed to stay in the definite window display area.

In the above case, information that will be preferentially displayed in each list when the list widths are reduced can be set to suit particular operational conditions or status of facilities.

In addition, even when the sample list is displayed in reduced form, for example whether absorbance of the sample has been measured or is currently being measured or the measurement itself has failed is displayed, the operator can confirm the particular measurement status of the sample without changing the current window to a subwindow.

Effects of the Invention

According to the present invention, since the display width of a list which displays details of desired data can be increased and since the display widths of other lists can be increased, the operator can confirm multiple kinds of data at the same time in the limited display area. This eliminates a need for a troublesome window change, thus reducing a burden upon a medical technologist who investigates causes of measured-data alarms and confirms detailed information on the data. In addition, even if the number of kinds of detailed information to be confirmed to seek for the causes of the measured-data alarms is increased, there is no need for the operator to learn new window operations, since the operator can confirm the detailed information in one window area.

BRIEF DESCRIPTION OF THE DRAWINGS

FIG. 2 shows an example of a window for confirming measurement results as well as samples whose absorbance was measured by the analyzer;

FIG. 3 shows an example of displaying a measurement result list at the highest level of detail;

FIG. 6 shows an example of horizontal sizes of a sample list and measurement result list and definitions of display items;

FIG. 9 shows another example of horizontal sizes of the sample list and measurement result list and definitions of display items.

MODE FOR CARRYING OUT THE INVENTION

Hereunder, an embodiment of the present invention will be described in accordance with the accompanying drawings.

Figure 1:
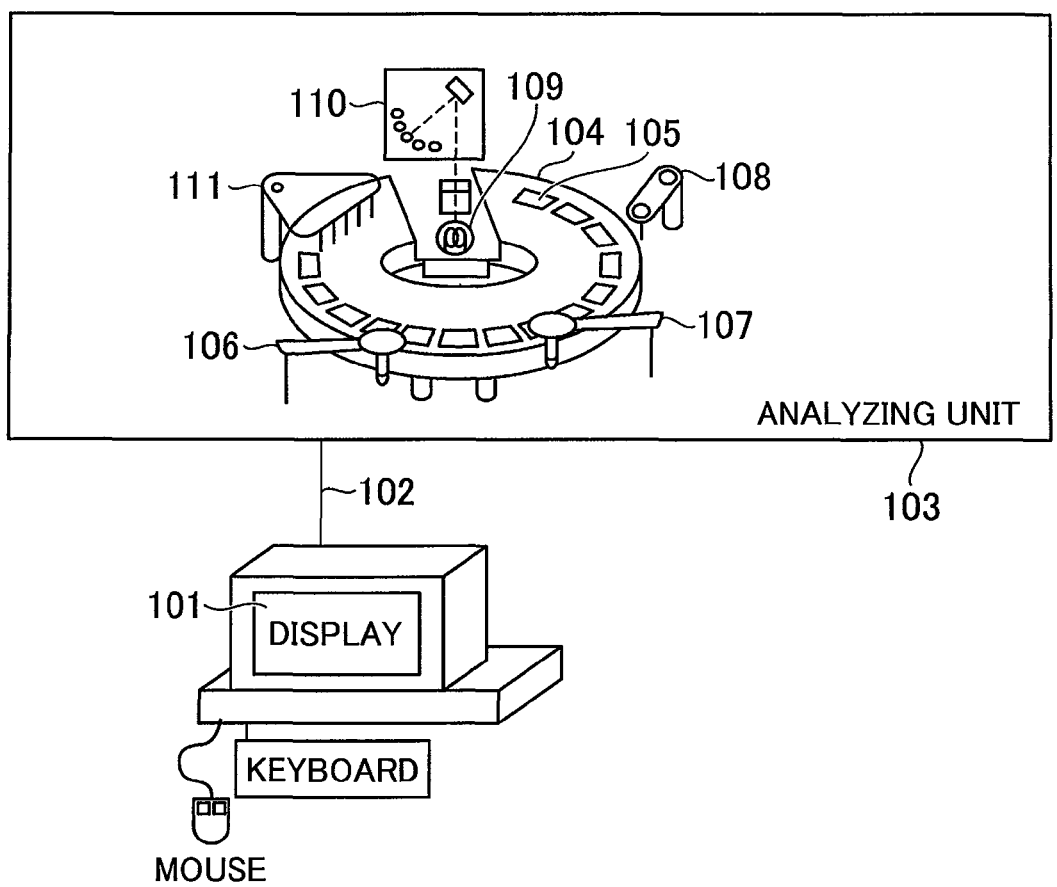
FIG. 1 is a schematic diagram of an automatic analyzer.

FIG. 1 is a schematic diagram showing an overall configuration of an automatic analyzer. The automatic analyzer is first outlined below.

Referring to FIG. 1, selecting an analytical measurement item relating to a sample, from an operating unit 101 that includes a display device and input devices such as a keyboard and mouse, and then pressing a starting button transmits an analytical measurement request to an analyzing unit 103 via an interface 102. In accordance with an analytical instruction, the analyzer, while rotating a reaction disk 104, dispenses the sample into reaction vessels 105 via a sample-dispensing probe 106, and after creating a reaction solution by dispensing a reagent via a reagent probe 107, stirs the reaction solution using a stirrer 108. The analyzer next measures absorbance of the reaction solution in each reaction vessel 105 using a light source 109 and a multiwavelength photometer 110, and then computes a concentration of a component pertinent to the selected analytical measurement item. After output of measurement results, the reaction vessel 105 is cleaned by a cleaning unit 111. The analyzing unit 103 transmits concentration computation results on the analytical item of the measured sample, absorbance data (reaction process data) that has been used to compute the concentration, reagent information, and calibration curve data to the operating unit 101 via the interface 102. An operator can use the display device of the operating unit 101 to confirm the measurement results relating to the analytical item of the sample whose measurement was requested, the reaction process data, the reagent information, and the calibration curve data.

FIG. 2 shows an example of a window for confirming measurement results as well as samples whose absorbance was measured by the analyzer. A sample list 201 and a measurement result list 202 are displayed at the same time in a definite data display area 203. This display is initially presented in sample details mode 701 shown in FIG. 7, with the sample list being displayed at the highest of three levels of detail. In accordance with a sample list definition table 601 of FIG. 6, a sample measurement status 204, a sample ID 205, a sample name 206, and a sample setup position number 207 are presented as display items in the sample list 201. In accordance with a measurement result list definition table 602 of FIG. 6, an analytical item name 209, a first test value 210, a retest value 211, a data alarm 212 relating to the first test value, and a data alarm 213 relating to the retest value are presented as display items in the measurement result list. A horizontal size corresponding to the highest level of detail is selected as width of the sample list, from the sample list definition table 601. A horizontal size corresponding to a middle level of detail is selected as width of the measurement result list, from the measurement result list definition table 602. Selection of a measurement result DETAIL button 214 by mouse operations changes the sample details mode 701, which is the initial display mode, to a measurement result details mode 702, as shown in a mode transition diagram of FIG. 7. Since the list widths corresponding to the measurement result details mode are then selected per FIG. 6, the width of the measurement result list is increased and that of the sample list is reduced. Another embodiment for changing the display mode from the sample details mode 701 to the measurement result details mode 702 is achievable by operating a scrollbar 208, instead of operating the measurement result DETAIL button 214. For example, while dragging the scrollbar 208 using the mouse, the operator may move the scrollbar 208 in a leftward direction for reduced width of the sample list 201. Upon the movement of the scrollbar 208 being completed, this triggers a display mode change from the sample details mode 701 to the measurement result details mode 702, as shown in the mode transition diagram of FIG. 7.

FIG. 3 shows an example in which the measurement result list 202 will be displayed at the highest level of detail in the measurement result details mode when the measurement result DETAIL button 216 is selected by the operator in FIG. 2. In accordance with the sample list definition table 601, only a sample measurement status 303 and a sample ID 304 are presented as display items in a sample list 301. In accordance with the measurement result list definition table 602, in addition to an analytical item name 305, a first test value 306, a retest value 307, a data alarm 308 relating to the first test value, and a data alarm 309 relating to the retest value, sample-dispensing time 310 corresponding to the first test value, and sample-dispensing time 311 corresponding to the retest value are presented as display items in a measurement result list 302. A horizontal size corresponding to a low level of detail is selected as width of the sample list, from the sample list definition table 601. A horizontal size corresponding to a high level of detail is selected as width of the measurement result list, from the measurement result list definition table 602. Mouse selection of any data in the measurement result list 302 displays a selection menu 314. Next mouse selection of a reaction process MONITOR button 315 from the selection menu 314 changes a current display mode from a measurement result details mode 702 to a measurement-related details mode 703, as shown in the mode transition diagram of FIG. 7, then reduces the width of the measurement result list, and displays a reaction process monitor. Selection of a RETURN button 312 returns the display mode from the measurement-related details mode 703 to the measurement result details mode 702, as shown in the mode transition diagram of FIG. 7, then displays the sample list 301 at a higher level of detail, and further returns the display mode to the initial display mode shown in FIG. 2.

Figure 4:
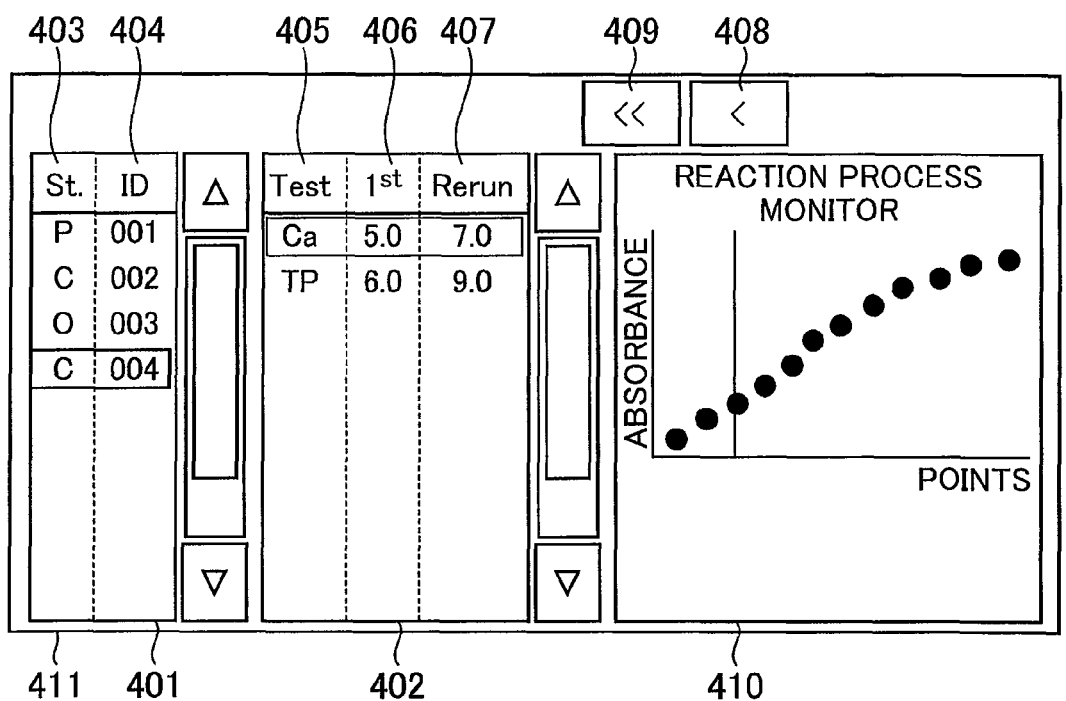
FIG. 4 shows an example of displaying a reaction process monitor at the highest level of detail.

FIG. 4 shows an example in which the reaction process monitor will be displayed at a low level of detail of the measurement result list 302 in the measurement-related details mode when the reaction process MONITOR button 315 is selected by the operator in FIG. 3. In accordance with the sample list definition table 601, only a sample measurement status 403 and a sample ID 404 are presented as display items in a sample list 401. In accordance with the measurement result list definition table 602, only an analytical item name 405, a first test value 406, and a retest value 407 are presented as display items in a measurement result list 402. A horizontal size corresponding to a low level of detail is selected as width of the sample list, from the sample list definition table 601. A horizontal size corresponding to a low level of detail is selected as width of the measurement result list, from the measurement result list definition table 602. A reaction process monitor 410 that displays absorbance data relating to data on an analytical item selected in the measurement result list 402 is displayed at the right side of the measurement result list 402. A horizontal size of display parts for displaying the reaction process monitor is calculated or determined by subtracting the width of the sample list 401 and that of the measurement result list 402 from a horizontal size of a data display area 411. An alternative to this method may be by defining a horizontal size of the reaction process monitor beforehand as shown in FIG. 6, and using the predefined value.

Figure 7:
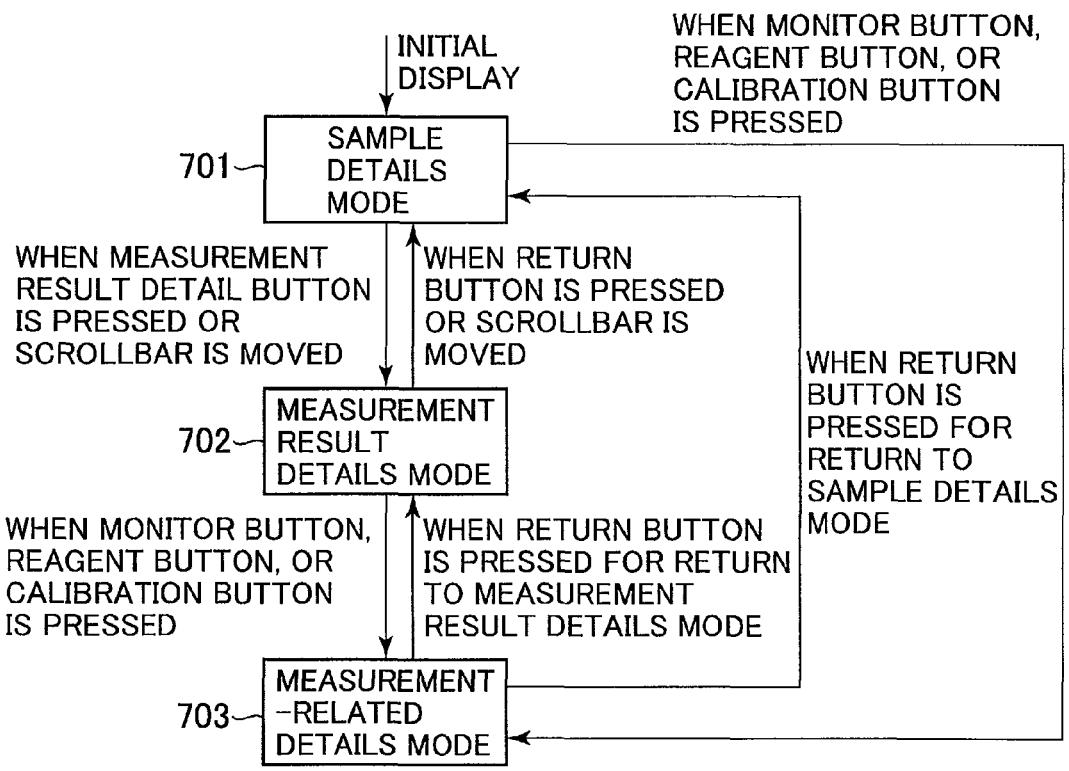
FIG. 7 shows an example of changes in states of display modes.

Selection of a RETURN button 408 for a return to the measurement result details mode returns the display mode from the measurement-related details mode 703 to the measurement result details mode 702, as shown in the mode transition diagram of FIG. 7, and then as shown in of FIG. 3, further returns the display to the display mode in which the measurement result list is displayed at the high level of detail. Selection of a RETURN button 409 for a return to the sample details mode returns the display mode from the measurement-related details mode 703 to the sample details mode 701, as shown in the mode transition diagram of FIG. 7, and then as shown in of FIG. 2, further returns the display to the display mode in which the sample list is displayed at the high level of detail. In addition, if another analytical item is selected in the measurement result list 402, absorbance related to the newly selected analytical item will be displayed in the reaction process monitor 410. Furthermore, the measurement status of the sample being displayed in the sample list 401 or the measurement result list 402, or the latest measurement result information on the analytical item can be displayed and confirmed in the reaction process monitor by updating the display of the list in real time.

Figure 8:
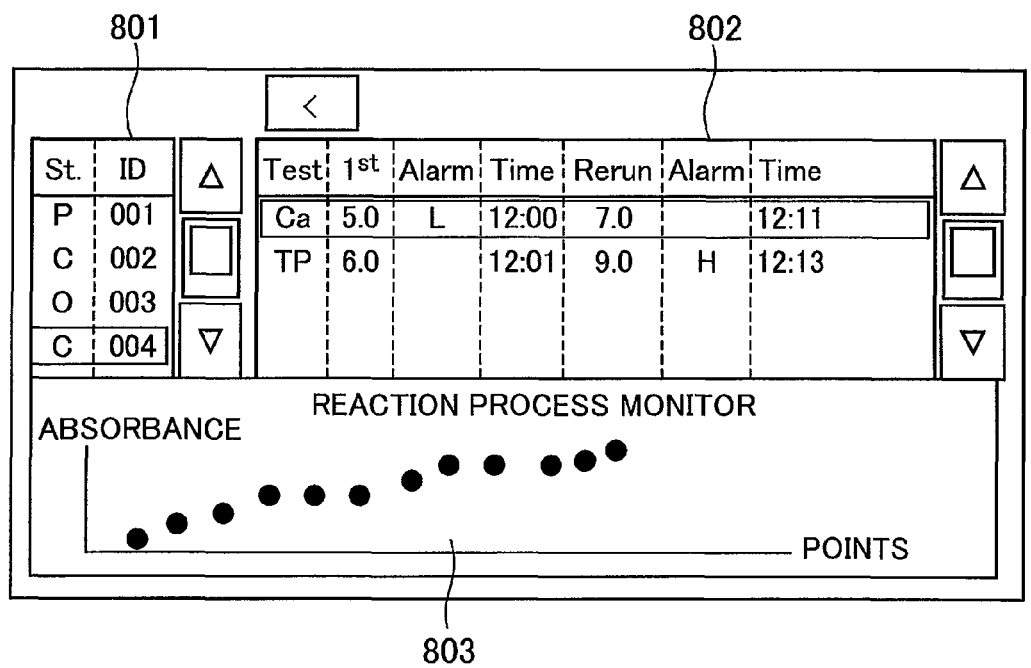
FIG. 8 shows another example of displaying a reaction process monitor at the highest level of detail.

FIG. 8 shows a second example of display in which the reaction process monitor will be displayed at the low detail level of display of the measurement result list 302 in the measurement-related details mode when the reaction process MONITOR button 315 is selected by the operator in FIG. 3. In accordance with a sample list definition table 901, only the sample measurement status 303 and the sample ID 304 are presented as display items in a sample list 801, as in FIG. 3. In accordance with a measurement result list definition table 902, the analytical item name 305, the first test value 306, the retest value 307, the first-test data alarm 308, the retest data alarm 309, the sample-dispensing time 310 corresponding to the first test value, and the sample-dispensing time 311 corresponding to the retest value are presented as display items in a measurement result list 802. A horizontal size corresponding to a low level of detail is selected as width of the sample list, from the sample list definition table 901. A vertical size corresponding to the low level of detail is selected as height of the sample list, from the sample list definition table 901. A horizontal size corresponding to a low level of detail is selected as width of the measurement result list, from the measurement result list definition table 902. A vertical size corresponding to the low level of detail is selected as height of the measurement result list, from the measurement result list definition table 902. The heights of the sample list and the measurement result list are small, compared with heights corresponding to middle levels of detail of the lists, and both lists are scaled down vertically.

A reaction process monitor 803 that displays absorbance data relating to data on an analytical item selected in the measurement result list 802 is displayed under the sample list 801 and the measurement result list 802. A vertical size of display parts for displaying the reaction process monitor is calculated or determined by subtracting the height of the sample list 801 from a vertical size of a data display area 804. An alternative to this method may be by defining a vertical size of the reaction process monitor beforehand as shown in FIG. 6, and using the predefined value.

FIG. 6 shows the tables that define relationships of the sample list and measurement result list with respect to the display mode, the widths and heights of the two lists, and the display items. These factors and elements of the sample list are defined in the sample list definition table 601, and those of the measurement result list are defined in the measurement result list definition table 602. In modes other than the display mode corresponding to the highest level of detail, the operator can specify any of the display items corresponding to the high level of detail. The display items underlined in FIG. 6 are displayed at all times during operation. In the example of FIG. 6, the sample measurement status is the item displayed at all times in the sample list, and the analytical item name in the measurement result list. In the measurement result details mode, the sample ID is specified to be displayed in the sample list. Specific sample IDs can be assigned on a facilities-by-facilities basis. In addition, the sample name may be specified instead of the sample ID.

Figure 5:
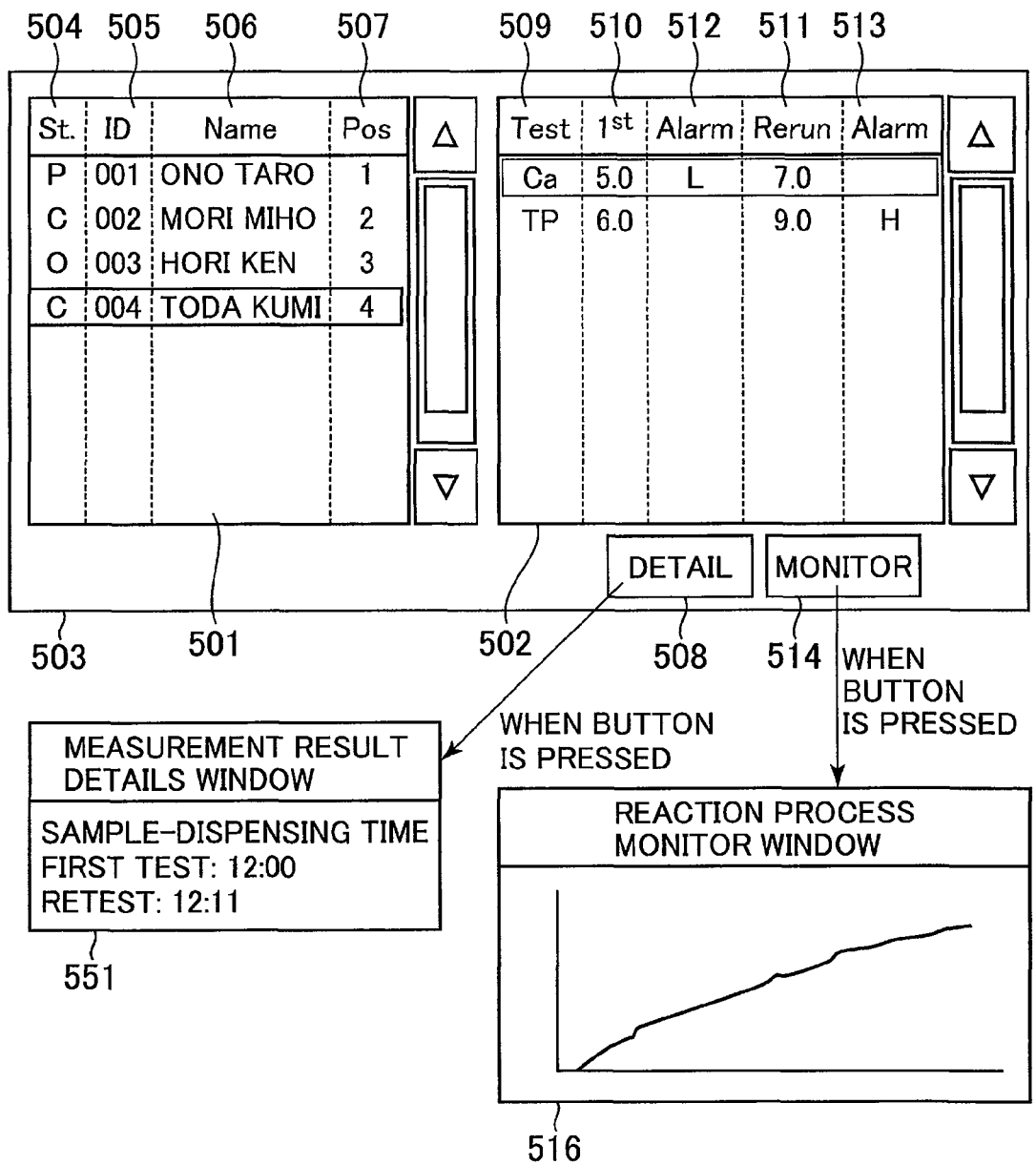
FIG. 5 shows an example of conventional windows for confirming samples and details of measurement results.

FIG. 5 shows an example of conventional display windows. In the foregoing example, a press of a measurement result DETAIL button 508 to confirm sample-dispensing time corresponding to a first test value and a retest value displays a measurement result details window 515 as a subwindow in overlapped form upon a sample list 501 and a measurement result list 502. After this display, closing the subwindow 515 and then pressing a reaction process MONITOR button 514 to confirm the reaction process monitor displays a reaction process monitor window 516 as a subwindow in overlapped form upon the sample list 501 and the measurement result list 502. To reconfirm reaction processes relating to a desired analytical item different from that selected in the measurement result list 502, the desired analytical item needs to be newly selected from a pull-down menu or the like, in the subwindow 516. In this way, repeated opening/closing of a subwindow or frequent window changes are needed to confirm detailed information on measurement results. In addition, since the subwindow 515 or 516 is displayed in overlapped form upon the sample list 501 and the measurement result list 502, even when the display of the sample list 501 and measurement result list 502 is updated, the operator has been unable to confirm this with the subwindow remaining open.

According to the present invention, provided that the display width of a list and the amount of information to be displayed in the list are changed according to the detail level of information to be confirmed, measurement result information on samples can be simultaneously displayed in one window without displaying a subwindow in overlapped form in the definite display area. Accordingly, there is no need to overlap a subwindow or change the current window to another window, as in conventional techniques, in order to confirm the detailed information relating to the measurement results. Even an inexperienced operator, therefore, can confirm details of measurement results without hesitating as to window switching.

In addition, if a function is provided that previously assigns information to be preferentially displayed in a list whose display width has been reduced, displaying the information for identifying samples at all times during operation to suit the particular operational status or operating needs of the facilities will improve working efficiency since the operator will be able to search for the samples easily and without changing the window, even when he or she wishes to shift to the confirmation of the detailed measurement result information relating to other samples. Furthermore, even when information other than sample information is displayed at the highest level of detail, the operator can confirm the measurement status of other samples by making a continuous display of changes in the measurement status of each sample, that is, whether the absorbance of the sample has been measured or is currently being measured or the measurement itself has failed.

While the present embodiment has assumed that lists are displayed as an example of parts for displaying sample information or measurement results, the technique according to the present invention can also be applied to using tables and other display parts instead of and as well as the lists.

DESCRIPTION OF REFERENCE NUMERALS

101 Operating unit
102 Interface
103 Analyzing unit
104 Reaction disk
105 Reaction vessel
106 Sample-dispensing probe
107 Reagent-dispensing probe
108 Stirrer
109 Light source
110 Multiwavelength photometer
111 Cleaning unit
201, 301, 401, 501, 801 Sample list
202, 302, 402, 502, 802 Measurement result list
203, 313, 411, 503 Data display area
204, 303, 403, 504 Sample measurement status
205, 304, 404, 505 Sample ID
206, 506 Sample name
207, 507 Sample setup position number
208 Scrollbar
209, 305, 405, 509 Analytical item name
210, 306, 406, 510 First test value
211, 307, 407, 511 Retest value
212, 308, 512 Data alarm relating to first test value
213, 309, 513 Data alarm relating to retest value
214, 508 Measurement result DETAIL button
310 Sample-dispensing time corresponding to first test value
311 Sample-dispensing time corresponding to retest value
312 RETURN button
314 Selection menu
315, 514 Reaction process MONITOR button
408 Button for returning to measurement result details mode
409 Button for returning to sample details mode
410, 803 Reaction process monitor
515 Measurement result details window
516 Reaction process monitor window
601, 901 Sample list definition table
602, 902 Measurement result list definition table
701 Sample details mode
702 Measurement result details mode
703 Measurement-related details mode

The invention claimed is:

1. An automatic analyzer, comprising:
   an analyzing unit analyzing components of a sample to obtain a measurement result of the sample;
   a computer including a processor and a memory device;
   a display device connected to the computer, the computer controlling the display device to display information in a plurality of categories, the plurality of categories including a sample list, a measurement result list of a sample in the sample list, and measurement details information,
   wherein the information displayed in the sample list category and the measurement result list category include one or more display items for each category, and the information displayed in the measurement details information category is information related to one of reaction process information indicating data of a measurement result of a sample, reagent information, and calibration curve data,
   wherein when a category is displayed on the display device, the information of the category is displayed within the pane of one window on the display device, the width of a pane is adjusted depending on a display mode, the information of two or more categories is displayed in the one window without being overwritten, and the display items displayed within each of the sample list category and the measurement result list category are displayed in accordance with a priority level stored in a definition table,
   wherein the definition table stored on the memory device defines the priority level related to displaying each of the one or more display items in each of the sample list category and the measurement result list category relating to the width of a respective pane for a respective category,
   wherein in a first display mode, the computer controls the display device to display the display items for the sample list category and the display items for the measurement result list category in the one window, the display items displayed in the sample list category are information about one or more samples, and the display items displayed in the measurement result list category are at least a name of an analytical item of a sample in the sample list and a measurement result of a sample in the sample list, and the width of the respective panes in the one window are adjusted by the computer so the display items within each category do not overwrite each other,
   wherein the computer receives an instruction, from an operator, for the computer to display on the display device one of reaction process information indicating data of a measurement result of a sample, reagent information, and calibration curve data, which each relate to a measurement result of a sample in the measurement result list,
   wherein once the instruction is received, the computer controls the display device to display information for each of the sample list category, measurement result list of a sample in the sample list category, and measurement details information category in a second display mode, the information displayed for the measurement details information is information corresponding to the received instruction,
   wherein, in the second mode, the width of the pane for at least the measurement result list category is reduced to be less than the width of the pane for the measurement result list category in the first mode, the display items displayed in each of the sample list category and measurement result list category are displayed in accordance with the priority in the definition table and the display items do not overwrite each other, and in the second display mode, the display items in the measurement result list category include at least the name of the analytical item of the sample, and the pane for displaying the measurement details information category corresponding to the received instruction is displayed adjacent to the pane for the measurement result list category, and
   wherein the information displayed in each of the categories displayed in the pane is updated in real time based on the progress of the analyzing unit obtaining measurement results for a sample regardless of receiving the instruction from the operator for updating the information.

2. The automatic analyzer according to claim 1, wherein for the category of the sample list, the display items include at least one item selected from the group consisting of a sample measurement status, a sample ID, a sample name, and a sample setup position number; and
   for the category of the measurement result list, the display items include at least one item selected from the group consisting of an analytical item name, a first test value, a retest value, a data alarm relating to the first test value, a data alarm relating to the retest value, sample-dispensing time corresponding to the first test value, and sample-dispensing time corresponding to the retest value.

3. The automatic analyzer according to claim 1, wherein the computer controls the display device to display a sample measurement status of the sample list, which is a display item, at all times in the sample list category.

* * * * *